United States Patent [19]

Gasic

[11] Patent Number: 4,588,587

[45] Date of Patent: May 13, 1986

[54] METHOD OF TREATMENT TO INHIBIT METASTASIS

[75] Inventor: Gabriel J. Gasic, Gulph Mills, Pa.

[73] Assignee: Pennsylvania Hospital, Philadelphia, Pa.

[21] Appl. No.: 471,197

[22] Filed: Mar. 1, 1983

[51] Int. Cl.[4] ............................................. A61K 35/62
[52] U.S. Cl. ................................................... 424/95
[58] Field of Search ......................................... 424/95

[56] References Cited

PUBLICATIONS

Gasic et al.,–Cancer Research, vol. 43, Apr. 1983, pp. 1633–1636.

Budzynski et al.–PSEBM, vol. 168, (1981), pp. 259 & 261–265.

Primary Examiner—Sam Rosen
Attorney, Agent, or Firm—Ratner & Prestia

[57] ABSTRACT

Method for treating a patient to inhibit metastasis of malignant cells by administering to the patient a therapeutically effective amount of a composition including a blood anticoagulant and a protease inhibitor. A composition apparently unique for this purpose is a leech salivary gland extract, the anticoagulant effect and protease inhibitory effect of which are believed to be significant. Other significant components may also be present in the leech salivary gland extract and these components may act synergistically in producing the observed antimetastatic effect.

11 Claims, No Drawings

METHOD OF TREATMENT TO INHIBIT METASTASIS

BACKGROUND OF THE INVENTION

This invention pertains to a method of treatment for inhibiting the spread of malignant cells, or metastasis.

"Metastasis", as used herein, is defined as the transfer of malignant tumor cells, or neoplasm, via preformed body vascular channels (blood vessels or lymphatics), or via natural body cavities, usually from the primary focus of neoplasia to a distant site in the body, and subsequent development of secondary tumors or colonies in the new location.

Metastasis is an ominous sign of malignancy and often represents a significant factor leading to death. Its treatment is difficult to achieve with conventional methods, such as surgery and radiotherapy. Efforts to treat cells in metastasis by a systematic therapy, such as the one proposed in this application, have heretofore been largely unsuccessful.

The mechanism by which metastasis occurs is believed to involve several steps, such as entry of tumor cells into the circulation (intravasculation); their transport by the blood stream; interactions of circulating malignant cells with platelets and plasma clotting factors with activation of the hemostatic system; interaction of the same cells with host cells other than platelets; arrest of tumor cells, surrounded by platelet aggregates and fibrin clots within capillaries; proteolytic attack of the blood vessel wall, particularly of its basement membrane, by tumor enzymes; escape from the circulation system (extravasculation); and formation of secondary tumors or colonies.

Blood sucking animals, such as leeches, mosquitoes and vampire bats have long been known to possess in their saliva substances which chemically interact with the blood or blood components. For this reason, leeches have been used for blood letting since antiquity. Although this practice achieved great popularity in Europe at the beginning of the last century and has since been abandoned, interest in the nature and properties of leech anticoagulants (one of the known components of the leech saliva which react with blood clotting factors) has recently been renewed as a consequence of the greater interest in the biochemistry of blood clotting and the search for new antithrombotic agents. These investigations have culminated in the isolation and characterization of several leech anticoagulants, such as hirudin, a specific thrombin inhibitor from the species *Hirudo medicinalis;* hementerin, a plasminogen activator from leeches of the species *Haementeria lutzi*, and hementin, a fibrinogen and fibrin degrading enzyme from leeches of the species *Haementeria ghilianii* and probably from leeches of the species *Haementeria officinalis*.

Studies of the salivary glands from Hirudo or Haementeria leeches have also revealed the presence of several kind of protease inhibitors, i.e., substances capable of neutralizing or inhibiting the degrading or digestive activity of proteins by conventional enzymes, such as trypsin, plasmin, chymotrypsin, elastase, cathepsins, etc.

With regard to possible use as antimetastatic agents, conventional anticoagulants, including heparin and *Bothrops atrox* venom (Atroxin); antiplatelet agents, such as aspirin; and inhibitors of proteolytic activity from various natural sources, such as leupetin, aprotinin, etc. have all been tested and studied (individually). And some of these agents have shown a marginal (but only marginal) capacity to inhibit metastatic activity.

Notwithstanding these studies, however, there remains a continuing need for a more effective antimetastatic treatment method.

It is the general object of the present invention to provide such a method.

More specifically, an object of this invention is to provide a method of treatment to inhibit metastasis, by administering a therapeutically effective amount of a composition apparently uniquely adapted to inhibit metastasis.

BRIEF DESCRIPTION OF THE INVENTION

This invention comprises a method for treating an animal to inhibit metastasis of malignant cells in the patient's body by administering to that patient a therapeutically effective amount of a composition including both a blood anticoagulant and a protease inhibitor or a specific anticoagulant or protease inhibitor present in a leech salivary gland extract. Preferably both the blood anticoagulant and protease inhibitor are extracted from leech salivary glands. This extract may be produced by freeze drying dissected leech salivary glands, homogenizing the freeze dried material in an aqueous solvent, centrifuging the homogenized freeze dried material and filtering the centrifuged material to remove particulate material therefrom. The solvent of choice is water buffered, for example, by 20 mM/1 Hepes (N-2-Hydroxyethyl Piperazine-N-Ethane Sulfonic Acid) and 10 mM/1 $CaCl_2$ at a pH on the order of 7.8.

The effectiveness of leech salivary gland extract as an anti-metastatic agent is believed to be due to a unique and complex combination of anticoagulants, protease inhibitors of various kinds, and possibly other constituents in the extract, all of which act additively or synergistically on one or several steps of the complex mechanism of metastasis. Fractions of this extract, alone or in combination with conventional anticoagulants and protease inhibitors may also be effective in inhibiting metastasis.

DETAILED DESCRIPTION OF THE INVENTION

Leech salivary gland extract, a complex mixture of active compounds, including among others, blood anticoagulants and protease inhibitors, has been found to markedly reduce the number of metastatic tumor colonies induced by intravenous injection of T241 sarcoma cells in mice.

A similar effect has been observed upon injection of certain carcinoma cells. The mechanisms of metastasis in these animals are believed to be very similar to those in humans. These tests are indicative that an effective method to inhibit the metastatic spread of malignant cells in animals may be provided by administering a therapeutically effective amount of leech salivary gland extract, or components thereof or combinations of other constituents similar thereto.

Tests to date have utilized salivary gland extract, or active fractions thereof, from leeches of Class Hirudinea, Order Rhychobdellida, Family Glossiphonidae and leeches of Class Hirudinea, Order Gnathobdellida, Family Hirudinidae, the main prototypes being represented, among other leeches, by *Haementeria ghilianii* and *Haementeria officinalis*, in the first case, and by *Hirudo medicinalis*, in the second.

How the leech salivary gland extract acts to inhibit metastasis is not yet fully known. However, the hemostatic system has been thought to contribute to metastasis formation by causing vascular arrest of tumor cells. It may be hypothesized therefore that the extract's capacity to inhibit coagulation, platelet aggregation or both is an important factor in the dramatic antimetastatic effect demonstrated. Although T241 sarcoma cells lack the ability to aggregate platelets in vitro directly, platelet aggregation may be induced by exposed collagenous components of the basement membrane and underlying connective stroma, following attack on the vascular lining by T241 sarcoma cells. Applicant has demonstrated that aggregation of rat platelets induced by bovine collagen can be inhibited in vitro by the salivary gland extract. Therefore, there is a significant possibility that the antimetastatic effect of the extract can also be mediated by in vivo inhibition of platelet aggregation produced by collagen of the vascular basement membrane.

For comparison, tests have been conducted to observe the antimetastatic action produced by conventional anticoagulants. For this purpose, mice were treated with conventional anticoagulants, such as heparin, or Atroxin, a *Bothropes atrox* venom, commercially available from Sigma Company of St. Louis, Mo. Atroxin is a fibrolytic agent, similar to at least one of the known anticoagulants in leech salivary gland extract. Administration of these conventional anticoagulants reduced only slightly the number of lung and mediastinal tumors in injected mice. Even when heparin was given at much higher doses and more frequently, the antimetastatic effects seen with the extract of the present invention could not be reproduced.

Another contributory mechanism in metastasis is extravasation of the malignant tumor cell, or escape from the blood circulation to form secondary tumors at distant sites from the primary neoplasia. Others have reported that the crossing of anatomical barriers such as epithelial cell and vascular basement membranes by tumor cells first requires proteolysis of these structures by the invading cells. This is probably caused by an enzyme secreted by tumor cells, which is capable of attacking components of the basement membrane, such as collagen, laminim, etc.

It is hypothesized therefore that the leech salivary gland extract utilized in the present invention, which contains various types of protease inhibitors, may block the basement membrane degrading capacity of the tumor cells, thus preventing tumor cell extravasation and metastasis formation. Tests in vitro indicate that crude extracts both from *Haementeria ghilianii* and *Haementeria officinalis* and a semipurified fraction from *Hirudo medicinalis* (Rs #5) can inhibit the digestion of two components of the vascular membrane (Type IV collagen and laminin) by T241 mouse sarcoma cells, supporting the above hypothesis. However, the particular protease inhibitors which inhibit digestion of these components have not yet been isolated.

One striking effect of leech salivary gland extract administration is the total suppression of neoplastic involvement of the mediastinum, which is invariably present in control mice. This result suggests that the extract is capable of inhibiting invasion of the lung lymphatics after sarcoma cells have escaped from the blood circulation, or that the extract blocks colonization of the mediastinum lymph nodes by a mechanism still undetermined.

The above conclusions and hypotheses are based on the results of experiments described below, in which are used the following materials and methods.

Tumor

Sarcoma T241 (12), a dimethylbenzanthracene-induced tumor originally derived from a C57BL/6 mouse, was maintained as ascitic tumor in syngeneic C57BL/6 mice or B6AF$_1$ compatible hybrids (Jackson Laboratory, Bar Harbor, Me.). The capacity of the cells of this tumor to induce platelet aggregation and coagulation was assayed in a conventional manner. Addition of up to $2 \times 10^6$ T241 cells to 500 ul of heparinized mouse or rat platelet-rich plasma (5–10 units heparin per ml) failed to aggregate platelets. The tumor cells, however, did display a moderate procoagulant activity as reflected by a shortened recalcified clotting time. The addition of $10^6$ T241 cells to syngeneic citrated plasma reduced the clotting time to between ⅓ and ½ control levels. Another known property of these cells is the capacity to degrade type IV collagen.

Model of Metastasis

Lung tumor colonies were induced by the intravenous injection of T241 sarcoma cells. One week-old ascitic tumor cells were separated by centrifugation (100 g for 10 min) at 4° C., washed twice with Hanks' solution and suspended in the same medium (125,000–250,000 cells per ml). The suspension contained monodispersed cells of high viability (95%). Two tenths of one ml of the suspension containing 25,000 or 50,000 cells were injected intravenously into male or female C57BL/6 mice (about 25 g), and into B6AF$_1$ mice (25–30 g), respectively, the animals housed under identical conditions of temperature, photoperiodicity, and feeding, were killed 20 days later and the number of metastases counted with a Bausch & Lomb dissecting microscope.

Preparation of Crude Salivary Gland Extract

Salivary gland extracts were prepared from freeze-dried anterior glands of Haementeria ghilianii and from anterior and posterior glands dissected from *Haementeria officinalis*. Glands were homogenized in 3 ml of aqueous solution containing 20 mM Hepes and 10 mM CaCl$_2$ per liter (pH 7.8) using a glass homogenizer, and the homogeneate centrifuged at $20,000 \times g$ for 15 minutes. The supernatant was saved and the pellet submitted to repeated extractions (with the same buffer) and centrifugation, using 2–3 ml of buffer for each extraction. After this procedure, the various supernatants were pooled and centrifuged at $100,000 \times g$ for 60 minutes. The resulting supernatant was then passed through a 0.22 micrometer pore filter, and their protein content determined by the Bio-Rad method, as recommended by the BIO-RAD company. The final concentration was readjusted to contain 2 mg protein per ml.

Fractionation of crude salivary gland extract from *Haementeria ghillianii*. The fraction containing hementin activity was precipitated with ammonium sulfate (70% saturation) and the precipitate separated by centrifugation at $8,000 \times g$ for 20 min. The supernatant were freeze dried and both the precipitate and the lyophilized supernatant was dissolved in about 6 ml of distilled water, placed in separate dialyzing tubes with a molecular weight cut off point of 3,500, and dialyzed against one liter of solution (20 mM Hepes, 10 mM CaCl$_2$ (pH 7.8 buffer)) with changes at 1, 3 and 24 hr.

After dialysis, the protein concentration of the two fractions was determined by the Bio-Rad method. Generally, 30% of the protein extract was in the precipitate and the remaining 70% was in the supernatant. The protein concentrations of both fractions were adjusted with buffered solution to a concentration of 2 mg/ml sterilized by Millipore filtration and stored at −70° C. Both fractions were tested for thrombin clotting activity, ability to inhibit various proteolytic enzmes (see below for methods), and capacity for inhibiting experimental metastasis. While protease inhibitors were present in both fractions, only the precipitate showed hementin activity, i.e., the capacity to prolong the thrombin clotting time. In further fractionation, an ammonium sulfate precipitate was dissolved in buffered solution applied to a DEAE anion exchange column (Whatman DE52), and protein eluted with a 0.01 to 0.15 M $CaCl_2$ gradient in 20 mM Hepes, 10 mM $CaCl_2$ (pH 7.8 buffer) aqueous solution. 5 ML fractions were collected. The elution profile showed two protein peaks, as measured by absorbance at 280 nm. The majority of proteins eluted in the void fraction (peak 1) with hementin activity appearing in the mid part of peak 2 (about 25 mM $CaCl_2$). The recovery at this step was about 50%. The void volume fraction, as well as the semipurified hementin fraction, were tested for clotting inhibitory activity, presence of protease inhibitors, and capacity to prevent tumor dissemination.

Preparation and fractionation of salivary gland extracts from Hirudo medicinalis. Since in this species a clean anatomical dissection of the glands in the neck region is not practical, crude extracts were prepared from the anterior part of the leech extending from the suctorial disc to approximately 5 mm in front of the anterior (male) genital orifice. Crude salivary gland extracts and several semipurified fractions were prepared by a a modification of the method of Markwardt (Methods in Enzymology, Vol. 19, pages 924–932, 1970). Briefly, dried leech heads, after dehydration with 96% ethanol for 48 hours, were extracted with 10 volumes of 40% acetone in water and centrifuged. The supernatant was separated from the pellet of leech heads (called Residue 1=Rs1) by centrifugation, its pH adjusted to 4.3 with glacial acetic acid, further extracted with 80% acetone in water, and centrifuged. The supernatant separated from the pellet (called Residue 2=Rs2) was treated with a diluted ammonium solution to pH 6.0. The volume was reduced to 1/10 of the original volume by placing the solution in a vacuum at 40°. Next, the concentrate was extracted with chloroform, and the organic phase separated from the aqueous extract. Evaporation of the organic phase led to a chloroform residue (called Rs4). The aqueous phase was centrifuged separating a supernatant from a pellet (called Residue 3=Rs3). The supernatant was concentrated in the vacuum, its pH adjusted to 1.8 with 10% trichloroacetic acid. The raw hirudin product was precipitated from 10 fold dilution with acetone, washed with acetone and the solvent removed in the vacuum. The raw hirudin preparation or crude extract had a specific activity of approximately 500 antithrombin units (AT-U) per ml. To obtain the residual fraction #5 (Rs5), a fraction with high activity against metastasis, the raw hirudin or crude salivary gland extract was dissolved in water and precipitated with 96% ethanol slowly added to the chilled solution containing 1 g of raw hirudin in 30 ml distilled water. The resulting precipitate, called residue #5, was removed by centrifugation, leaving the main bulk of hirudin in solution or supernatant. Rs5 was further purified by two more extractions with ethanol, removing most of its hirudin content. The hirudin preparation containing 10–15% pure hirudin, was further purified by gel filtration and ion-exchange chromatography.

Treatment of Mice with Salivary Gland Extract

Two tenths of one ml of extract or semipurified fractions (100–400 ug of protein) were injected intravenously through the tail vein two hours before and two and four hours after receiving the tumor cell inoculation. Controls were similarly injected, but with 20 mM Hepes, 10 mM $CaCl_2$, pH 7.8 aqueous solution. Additional controls were treated with either one intravenous injection of 15 units of heparin (Elkins-Sinn, Cherry Hill, N.J.) or 2 units of *Bothrops atrox* venom (Atroxin, Sigma, St. Louis, Mo.) in 0.2 ml of saline given 1 hour before tumor inoculation.

Assay of Protease Inhibitors in Crude Extract

Various amounts of crude extract were assayed for their ability to inhibit trypsin, plasmin, chymotrypsin, and granulocyte elastase using chromophoric or flourescent substrates. Reactions were allowed to proceed in the presence and absence of extract to determine the percent inhibition. (a) Trypsin Inhibitor Assay—After prewarming to 37° C., 50 microliters of a 40 micrograms/ml trypsin solution was added to a solution of 0.55 ml buffer (0.1 M Tris-HCl buffer, 20 mM $CaCl_2$, pH 7.8) 0.2 ml of substrate N-Benzoyl-DL-Arginine-p-Nitroanalide (Sigma, St. Louis, Mo.; 1 mg/ml $H_2O$) and salivary gland extract. Ten minutes later, the reactions were stopped by the addition of 0.2 ml 50% acetic acid and read in a spectrophotometer (Spectronic 710, Bausch & Lomb, Rochester, N.Y.) at 405 nm against a blank which contained all of the above components except the enzyme. (b) Plasmin Inhibitor Assay: Fifty microliters of porcine blood plasmin (Sigma; 40 micrograms/ml $H_2O$) was added to a 37° C. solution containing 0.55 ml of 0.05 M Tris-HCl buffer, pH 7.4 with 12 mM NaCl, 0.2 ml of Kabi substrate S2251 (Kabi, Greenwich, Conn.; 3 mM in $H_2O$), and salivary gland extract. After 10 minutes of incubation, 0.2 ml. of 50% acetic acid was added and the reactions were read as above. (c) Chymotrypsin Inhibitor Assays: To a 37° C. solution containing 0.35 ml buffer (0.1 Tris-HCl buffer pH 8.3 with 0.96 M NaCl), 0.2 ml of the Kabi substrate S2586 (0.6 mM in $H_2O$), and salivary gland extract, 50 microliters of chymotrypsin (400 ng/ml) was added. After 4 minutes, 0.2 ml of 50% acetic acid was added and samples were read as above. (d) Elastase Inhibitor Assay: Inhibition of granulocyte elastase by salivary gland extract was assayed using a fluorometric method. Elastase attack of the substrate N-t-BOC-Ala- Pro-Val-AMC split off 4 Methyl Coumaryl Amide (AMC) and the fluorescense emitted by this free group is recorded by an Amicon-Bowman Spectrofluoro- meter.

Study of the Anticoagulant Activity of the Salivary Gland Extract

C57Bl/6J male mice were injected intravenously with 0.2 ml salivary gland extract (2 mg/ml protein) or 0.2 ml buffer and bled from the heart 2, 4 and 6 hours after treatment. Nine parts of blood were mixed with 1 part of 3.2% sodium citrate and plasma from each mouse separated by centrifugation in an Eppendorf ultracentrifuge (8,000 g for 2 min). Recalcified and thrombin clotting time were performed by adding to aliquots of 0.1 ml of plasma, prewarmed at 37° C. for 3 minutes, 0.1 ml 25 nM CaCl, and 0.1 ml of thrombin solution, respectively. The thrombin of human origin (Sigma, St. Louis, Mo.) was reconstituted with water and diluted 1:1 with saline.

Assay of the Antiplatelet Activity of the Salivary Gland Extract

B6AF$_1$ female mice were injected intravenously with 0.2 ml of salivary gland extract (2 mg/ml protein) or 0.2 ml buffer and bled from the heart 2, 4 and 6 hours after treatment. Platelet-rich plasma was prepared from heparin-anticoagulated blood (5 units per ml) and the response of the platelets to tumor material in an aggregometer by adding 50 ul of plasma membrane vesicles (50 ug protein) from 15091A tumor cells to 450 ul of platelet-rich plasma. The activity of the extract against platelet aggregation induced by collagen was tested in vitro by using heparinized rat platelet-rich plasma (10 units/ml heparin) and acid soluble collagen prepared from bovine Achilles tendon (Worthington, Freehold, N.J.). For this purpose 400 ul of platelet-rich plasma were incubated at 37° C. with 50 ul of salivary gland extract (2 mg/ml protein). After 20 minutes of incubation, 50 ul of various dilutions of collagen in saline were added and platelet aggregation recorded with a Payton aggregometer (Buffalo, N.Y.).

of untreated rat controls responded with a typical aggregation to the various doses of collagen (lag period from 0.2 to 0.6 minutes), platelets incubated with the extract were totally unresponsive to the same aggregation stimulus.

Inhibitory Effect of the Salivary Gland Extract on Lung Tumor Colonies

Intravenous injection of T241 sarcoma cells into syngeneic or compatible hybrid mice regularly produced numerous lung tumor colonies and neoplastic involvement of the mediastinal lymph nodes. No metastasis were observed in other organs. Three intravenous injections of the salivary gland extract, given on the same day as tumor inoculation to C57BL/6J mice, reduced the percentage of animals developing mediastinal and lung tumors from 100 to 0, and 100 to 47 respectively (see Table 1).

Furthermore, those mice that did develop pulmonary metastases had far fewer tumors in number and their tumors were significantly smaller. The leech extract treatment was equally effective in B6F$_1$ mice. In this group of animals, three intravenous injections of extract totally suppressed mediastinal lymph node metastases and dramatically reduced the median number of lung tumor colonies per mouse from 61 to 3 (see Table 1). Likewise, the average diameter of the lung tumor colonies was diminished to half that of the untreated group.

TABLE 1

Effect of Leech Salivary Gland Extract from *Haementeria ghilianii* on Lung and Mediastinal Colonization Produced by Intravenous Injection of T241 Sarcoma Cells

| Treatment | Percentage of Mice with Tumors | | Lung Tumors per Mouse[a] | | $p^b$ | $p^c$ | Diameter of Lung Tumors[a] (mm[d]) |
|---|---|---|---|---|---|---|---|
| | Mediastinal | Lung | Median | Range | | | |
| 1. C57BL/6J Mice | | | | | | | |
| Control (Tris-HCl buffer) | 100 | 100 (30)[e] | 8 | 1–25 | | | 2.3 ± 0.1 |
| Salivary gland extract | 0 | 47 (30) | 2 | 1–3 | .001 | .001 | 1.4 ± 0.1 |
| Heparin | 80 | 100 (10) | 5 | 5–8 | N.S. | N.S. | 2.2 ± 0.1 |
| Atroxin | 70 | 100 (10) | 4 | 1–10 | N.S. | .05 | 2.2 ± 0.3 |
| 2. B6AF$_1$ Mice | | | | | | | |
| Control (Tris-HCl buffer) | 100 | 100 (13) | 61 | 22–87 | | | 2.7 ± 0.2 |
| Salivary gland extract | 0 | 100 (10) | 3 | 1–9 | .001 | .001 | 1.3 ± 0.1 |

[a]Excluding mice without lung tumors.
[b]Probability of no difference, in percentage of mice with mediastinal tumors, between treated and control mice.
[c]Probability of no difference, in number of lung tumors, between treated and control mice.
[d]Mean and S.E.M.
[e]Number between brackets = number of mice per group.
N.S. = not significant.

Inhibitory Activity of the Salivary Gland Extract Against Proteolytic Enzymes

The performed assays demonstrated the presence of inhibitors against trypsin, plasmin, chymotrypsin, and granulocyte elastase. To produce 50% inhibition of each enzyme activity, the average amounts of extract needed were 35, 9, 23 and 3 micrograms of protein respectively. A minimum of 3–5 assays were performed with each enzyme.

Inhibitory Effect of the Salivary Gland Extract on Coagulation and Platelet Aggregation The in vivo administration of the extract prolonged both the thrombin and the recalcified clotting time with a greater effect on the latter. When blood was drawn at 2, 4 and 6 hours after treatment, the extract also inhibited platelet aggregation induced by plasma membrane vesicles shed by the murine mammary adenocarcinoma 15091A, an effect that lasted for 2 to 4 hours after intravenous administration of the extract. While the platelets In Table 2 results of 9 additional experiments are reported, using salivary gland extracts from *Haementeria ghilianii* (Experiments 1, 2, 3, and 6), *Haementeria officinalis* (Experiment 9), and *Hirudo medicinalis* (Experiment 7). In every case, the extract significantly reduces the frequency (Table 2, column 1, 2) and size (Table 2, column 3) of lung tumor colonies and totally suppresses the neoplastic invasion of the mediastinum (Table 2, column 1), as compared with controls. Certain semipurified fractions, such as the 70% ammonium sulfate precipitate from *Haementeria ghilianii* (Experiment 4), and fraction Rs#5 from Hirudo medicinalis (Experiment 8) were almost as active as the crude extracts against metastasis by T241 sarcoma cells. Other fractions, such as the void volume collected at the beginning of DEAE cellulose column chromatography of crude extracts from *Haementeria ghilianii*, displayed less antimetastatic activity (Experiment 5). The activity of this extract could partially be inhibited by adding 1 M sodium phosphate to the crude preparation (Experiment 6).

Table 2 also reports the capacity of extracts and semipurified fractions to inhibit the activity of different proteolytic enzymes (columns 4, 5, 6, 7, 8), clotting (columns 9, 10) and platelet aggregation (column 11) in in vitro tests.

TABLE 2

EFFECTS OF SALIVARY GLAND EXTRACTS AND SEMIPURIFIED FRACTIONS FROM HAEMENTERIA GHILIANII, HIRUDO MEDICINALIS AND HAEMENTERIA OFFICINALIS ON EXPERIMENTAL MOUSE METATASES, PROTEASES, AND HEMOSTATIC ACTIVITY

| | | 1 % Mice With Tumors | | 2 Lung Tumors Per Mouse[a] | | 3 Size of Lung Tumors[a] (mm) | 4 Trypsin | 5 Plasmin | 6 Chymotr | 7 Elastase | 8 Thrombin | 9 Clotting Time[c] Recalcified (sec) | 10 Clotting Time[c] Thrombin (sec) | 11 Platelet Aggregation (%) |
|---|---|---|---|---|---|---|---|---|---|---|---|---|---|---|
| Experiment | Treatment | Lung | Mediastinal | Median | Range | | | | μg Protein to Product 50% Inhibition[c] | | | | | |
| | *Haementeria ghilianii's* Preparations | | | | | | | | | | | | | |
| 1 | Control | 100 (30) | 100 | 8 | (1-25)[b] | 2.3 ± 0.8 | | | | | | 53 ± 2 | 10 | 80 |
| | Crude extract | 45 (30) | 0 | 2 | (1-3) | 1.4 ± 0.3 | 35 ± 15 | 13 ± 5 | 23 ± 8 | 3 | | 250 | 250 | 0 |
| 2 | Control | 100 (13) | 100 | 61 | (22-87) | 2.7 ± 0.3 | | | | | | | | |
| | Crude extract | 100 (9) | 0 | 3 | (1-9) | 1.3 ± 0.3 | | | | | | | | |
| 3 | Control | 100 (26) | 96 | 17 | (1-80) | 3.0 ± 0.8 | | | | | | | | |
| | Crude extract | 45 (11) | 0 | 3 | (2-8) | 2.1 ± 0.4 | | | | | | | | |
| 4 | 70% AS Ppt[d] | 31 (13) | 0 | 2 | (1-4) | 1.8 ± 0.6 | 25 ± 5 | 14 ± 7 | 24 | 12 | | 250 | 250 | |
| | 70% AS Spn[d] | 100 (5) | 40 | 9 | (2-14) | 3.3 ± 1.2 | 39 | 8 ± 3 | 20 | | | 4 | | |
| 5 | Control | 100 (13) | 100 | 22 | (12-80) | 3.3 0.9 | | | | | | | | |
| | Void volume[e] | 100 (15) | 15 | 5 | (1-19) | 2.4 0.8 | 44 ± 17 | 300 | 300 | 116 | | 250 | 250 | |
| 6 | Control | 100 (6) | 100 | 129 | (120-138) | 3.0 ± 0.3 | | | | | | | | |
| | Crude extract | 83 (6) | 0 | 2 | (1-12) | 1.8 ± 0.6 | | | | | | | 46 | |
| | Part. In-activated Crude Extract w/1 M NaPO₃ | 100 (5) | 60 | 14 | (3-28) | 3.8 ± 0.1 | | | | | | | | |
| | *Hirudo Medicinalis's* Preparations | | | | | | | | | | | | | |
| 7 | Control | 100 (10) | 100 | 7 | (3-8) | 1.9 ± 0.6 | | | | | | | | |
| | Crude Extract | 70 (10) | 0 | 1 | (1-4) | 2.4 ± 1.1 | | | | | | | | |
| 8 | Control | 100 (30) | 100 | 13 | (1-97) | 3.1 ± 1.0 | | | | | | | | |
| | Fraction RS #5 | 50 (30) | 0 | 1 | (1-10) | 2.0 ± 1.0 | 7 ± 3 | 16 | 5 ± 2 | 11 | 39 | | 150 | |
| | *Haementeria officinalis's* extract | | | | | | | | | | | | | |
| 9 | Control | 100 (6) | 100 | 77 | (52-110) | 4.2 ± 0.8 | | | | | | | 15 | |
| | Crude extract | 100 (6) | 0 | 1 | (1-4) | 1.2 ± 0.7 | 10 | 24 | 23 | | | | 150 | |

[a]Excluding mice without metastases.
[b]Numbers in parentheses = number of mice.
[c]Mean S.D.
[d]Fractions resulting from ammonium sulfate precipitation (70% saturation) of the crude extract.
[e]Fraction collected at the beginning of the DEAE-cellulose column crompatography of the applied crude extract.

Thus, while somewhat purified fractions which are richer or leaner in one of the activities displayed by the crude leech extract, may show some antimetestatic activity, the best effect seems to be obtained when the two activities are present together. This suggests that the preferred embodiment of the present invention is the crude extract including the combination of active agents in a more or less "cocktail" mixture of which protease inhibitors and anticoagulants, perhaps peculiar to the leech extract, appear to be the more active constituents. It may be however that other components of the extract also participate in different degree. Further, a specific anticoagulant in leech extract may be combined with protease inhibitors from other sources and protease inhibitors found in leech salivary gland extract may be combined with anticoagulants from other sources to simulate the cocktail effect of the natural extract.

Efforts by others to interdict metastasis by the use of various types of conventional protease inhibitors and anticoagulants in different experimental models have not produced clear cut results. These agents appear to be far less active than the leech salivary gland extract utilized in the present invention, which confirms that by far the preferred embodiment of the present invention is that in which leech salivary gland extract is used.

To date, further characterization of leech salivary gland extract or fractions thereof has not been completed. However, it is known that among the components of these extracts, the protease inhibitors, which appear in high concentration, are indicated to be polypeptides of 6,000 to 40,000 daltons in molecular weight. These inhibitors have been shown to be effective in inhibiting protein degradation by various enzymes including trypsin, plasmin, chymotrypsin, elastases, cathepsins, kallikrein, and others.

From all of the foregoing, the overall observation that can be made is that an effective method for treating an animal to inhibit metastasis of malignant cells may be provided. This method comprises administering to the animal a therapeutically effective amount of a salivary gland extract from the South American leech *Haementeria Ghilianii*, or other leeches as indicated above. This has been demonstrated by intravenous inoculation of mice with T241 sarcoma cells either substantially contemporaneous with or prior to inoculation with the leech extract. Colonization of the mediastinal lymph nodes is substantially suppressed and the number of lung colonies produced is markedly reduced. The active antimetastatic material in the leech salivary gland extract and its functional mechanism remains to be established. It has been demonstrated that the extract effectively inhibits blood coagulation and platelet aggregation. Accordingly, one mechanism for the antimetastatic effect may be interference with hemostasis dependent tumor cell arrest in the microcirculation. A second and more important mechanism may be the prevention of tumor cell extravasation resulting from the extract's high content of protease inhibitors.

Other protease inhibitors and other blood anticoagulants in combination with leech salivary gland components may be similarly effective. Moreover, the specific protease inhibitors and blood anticoagulants in leech salivary gland extracts may be unique in their ability to arrest metastasis.

While the present invention has been described with respect to specific embodiments thereof, the appended claims are not intended to be limited thereto. Rather, it is intended that these claims be construed to encompass the present invention and all of its possible modes and variations, including such variations and modifications of the embodiments described above, which may be devised by those skilled in the art but which are within the true spirit and scope of the present invention.

I claim:

1. Method for treating an animal to inhibit metastasis of malignant cells, said method comprising administering to said animal a therapeutically effective amount of a composition comprising leech salivary gland extract derived by homogenization and solubilization, in aqueous solution, of leech salivary gland tissue and thereby isolating a product having antimetastatic properties.

2. Method as recited in claim 1, wherein said tissue is from a leech specie selected from the group consisting of *Hirudo medicinalis, Hamementeria officinalis,* and *Haementeria ghilianii.*

3. Method as recited in claim 1, wherein said specie is *Hirudo medicinalis.*

4. Method as recited in claim 1, wherein said specie is *Haementeria officinalis.*

5. Method as recited in claim 1, wherein said specie is *Haementeria ghilianii.*

6. A method as recited in claim 1, wherein said composition is the product of a process comprising freeze-drying dissected leech salivary glands, homogenizing said freeze-dried material in an aqueous solvent, centrifuging said homogenized material, and filtering the supernatant from said centrifuging process to remove particulate material therefrom.

7. A method as recited in claim 6 wherein said solvent is an aqueous solution comprising 20 mH Hepes and 10 mM CaCl$_2$ per liter.

8. The method of claim 1 wherein said composition includes at least one protease inhibitor.

9. The method of claim 1 wherein said composition contains a blood anticoagulant.

10. The method of claim 1 wherein said composition contains a blood anticoagulant and at least one protease inhibitor.

11. The method of claim 1 wherein the composition is administered by intravenous injection.

* * * * *